United States Patent [19]

Shun-Hsien

[11] Patent Number: 5,456,276
[45] Date of Patent: Oct. 10, 1995

[54] CONTACT LENS CLEANING APPARATUS

[76] Inventor: Wang Shun-Hsien, 5F, No. 311, Fu Kuo Road, Shih Lin, Taipei, Taiwan

[21] Appl. No.: 366,742

[22] Filed: Dec. 30, 1994

[51] Int. Cl.⁶ .................................................. B08B 3/04
[52] U.S. Cl. ................ 134/140; 134/158; 134/901; 185/38; 74/5.1
[58] Field of Search ...................... 134/158, 164, 134/161, 140, 143, 901; 185/38; 74/5.1

[56]  References Cited

U.S. PATENT DOCUMENTS

| | | | |
|---|---|---|---|
| 2,891,405 | 6/1959 | Elmore | 74/1.5 |
| 3,623,175 | 11/1971 | Emerson | 185/38 |
| 4,826,001 | 5/1989 | Castillo | 134/901 |
| 4,881,621 | 11/1989 | Ishida | 185/38 |
| 4,957,130 | 9/1990 | Lee | 134/158 |
| 5,232,003 | 8/1993 | Wei et al. | 134/901 |

*Primary Examiner*—Frankie L. Stinson

[57]  ABSTRACT

A contact lens cleaning apparatus having a clockwork controlled by a rotary knob to turn a ratchet wheel against a pawl, causing the lens cage to oscillate in the cleaning solution in the container, wherein the lens cage consists of two symmetrical semispherical gratings hinged together and retained in the closed position by a fastener for carrying the left eye contact lens and the right eye contact lens respectively.

2 Claims, 4 Drawing Sheets

CONTACT LENS CLEANING APPARATUS

BACKGROUND OF THE INVENTION

The present invention relates to a contact lens cleaning apparatus which uses a clockwork to oscillate a lens cage in the cleaning solution in a container, which lens cage is comprised of two symmetrical halves for holding the left eye contact lens and the right eye contact lens respectively.

Contact lenses must be regularly cleaned to prevent contaminations. If cleaning contact lenses with water or a cleaning solution by hand, the lens surface will be damaged easily and, a secondary contamination problem tends to happen. FIG. 1 shows a contact lens cleaning apparatus designed for cleaning contact lenses without direct contact of the hands. This structure of contact lens cleaning apparatus comprises a container to hold a cleaning solution, a bottom cover covered on the container, a lens cage suspended in the container, a top cover covered on the bottom cover and having an internal gear, a rotary knob having a bottom rod inserted through a hole on the top cover and a hole on the bottom cover and then coupled to the lens cage, a sun gear fixedly mounted around the bottom rod of the rotary knob, and a planet gear meshed between the sun gear and the internal gear. When the rotary knob is rotated, the lens cage is turned in the cleaning solution, and therefore the contact lenses are cleaned. The lens cage has two openings at the bottom through which contact lenses can be inserted into or taken out of the lens cage. This structure of contact lens cleaning apparatus is still not satisfactory in function. One drawback of this structure of contact lens cleaning apparatus is that the lens cage be turned in the cleaning solution only when the rotary knob is rotated with the hand. If the lens cage is not turned by the rotary knob, the contact lenses in the lens cage are simply dipped in the cleaning solution, and a satisfactory cleaning effect will not be achieved. Another drawback of this structure of contact lens cleaning apparatus is that lens cage is not openable and simply marked with L and R marks for the recognition of the contact lenses, and the user tends to make a mistake in wearing the contact lenses.

There is also known an electric contact lens cleaning apparatus which can automatically clean contact lenses. However, electric contact lens cleaning apparatus are commonly huge and expensive. When an electric contact lens cleaning apparatus is operated, the lens cage is turned at a high speed, and the lens surface of the contact lenses tends to be deformed. Furthermore, if an electric contact lens cleaning apparatus uses battery power supply to drive the mechanism, it will cause environmental pollutions.

SUMMARY OF THE INVENTION

The present invention has been accomplished under the circumstances in view. It is one object of the present invention to provide a contact lens cleaning apparatus which can automatic clean the contact lenses. It is another object of the present invention to provide a contact lens cleaning apparatus which does not consume electric power supply. It is still another object of the present invention to provide a contact lens cleaning apparatus which turns the lens cage in the cleaning solution smoothly without causing the contact lenses to deform. It is still another object of the present invention to provide a contact lens cleaning apparatus which does not cause any environmental pollution because it eliminates the use of a battery.

According to one aspect of the present invention, the contact lens cleaning apparatus uses a clockwork controlled by a rotary knob to turn a ratchet wheel against a pawl, causing the lens cage to oscillate in the cleaning solution in the container. According to another aspect of the present invention, the lens cage is comprised of two symmetrical semispherical gratings hinged together and retained in the closed position by a fastener for carrying the left eye contact lens and the right eye contact lens respectively.

DETAILED DESCRIPTION OF THE PREFERRED EMBODIMENT

Figure 1:
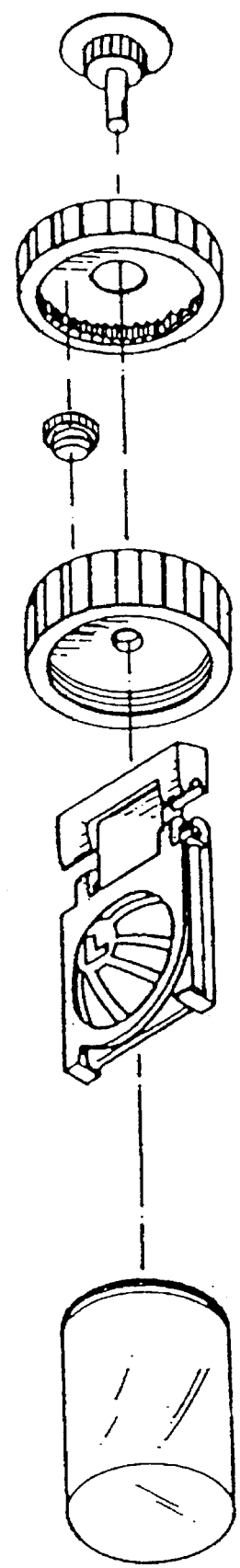
FIG. 1 is an exploded view of a contact lens cleaning apparatus according to the prior art.
Figure 2:
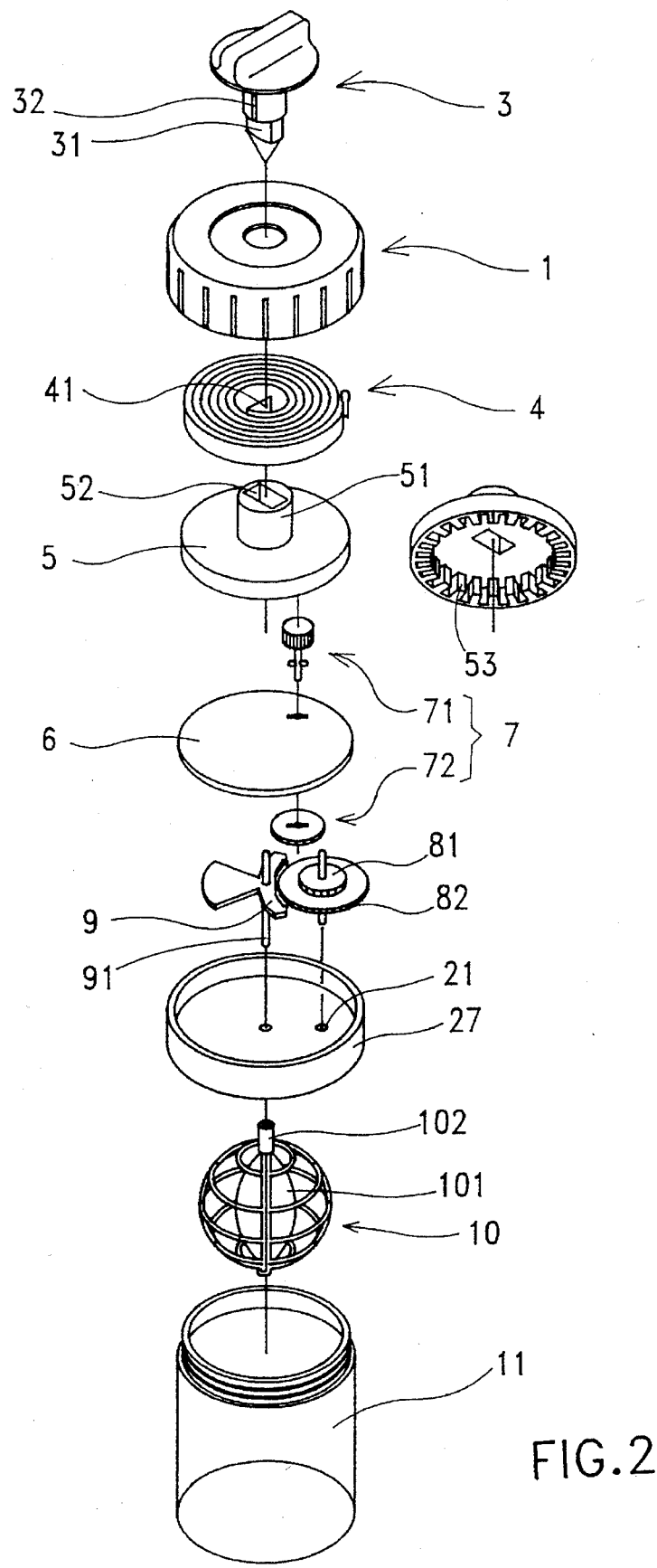
FIG. 2 is an exploded view of a contact lens cleaning apparatus according to the present invention.

Referring to FIG. 2, a contact lens cleaning apparatus in accordance with the present invention is generally comprised of a top cover 1, a bottom cover 2, a container 11, and a lens cage 10. The top cover 1 has a center through hole 11, which receives the driving rod 31 of a rotary knob 3. A clockwork 4 is received inside the top cover 1 around the driving rod 31 of the rotary knob 3, having a center tip 41 fixed to a retaining hole 32 on the driving rod 31 of the rotary knob 3. The square bottom end of the driving rod 31 is fitted into a square hole 52 on the top stub rod 51 of a rotary wheel 5. The rotary wheel 5 has a unitary internal gear 53 at the bottom and meshed with a first gear set 7. The first gear set 7 comprises a pinion 71 mounted on a locating board 6 and meshed with the internal gear 53, a big gear 72 fixedly mounted around the gear shaft of the pinion 71 and meshed with a second gear set 8. The second gear set 8 is mounted on a locating hole 21 on the bottom cover 2, comprised of a pinion 81 meshed with the big gear 72 of the first gear set 7, and a ratchet wheel 82 coupled with a driven pawl 9. The driven pawl 9 is coupled with a shaft 91. The shaft 91 inserts through a hole 22 on the bottom cover 2 and coupled to the axle holder 102 of the lens cage 10. The lens cage 10 is comprised of two semispherical gratings hinged together, an oval core 101 coupled to the axle holder 102. A fastener 103 is made on the lens cage 10 at the bottom to fasten the two semispherical gratings of the lens cage 10 in the closed position.

The aforesaid clockwork 4, locating board 6, rotary wheel 5, first gear set 7, and second gear set 8 are mounted within the bottom cover 2 and covered by the top cover 1. When the top and bottom covers 1 and 2 are fastened together, the bottom cover 2 is fastened to the container 11 by a screw joint to suspend the lens cage 10 in the container 11.

The aforesaid clockwork 4, locating board 6, rotary wheel 5, first gear set 7, and second gear set 8 are mounted within the bottom cover 2 and covered by the top cover 1. When the top and bottom covers 1 and 2 are fastened together, the bottom cover 2 is fastened to the container 11 by a screw joint to suspend the lens cage 10 in the container 11.

Figure 4:
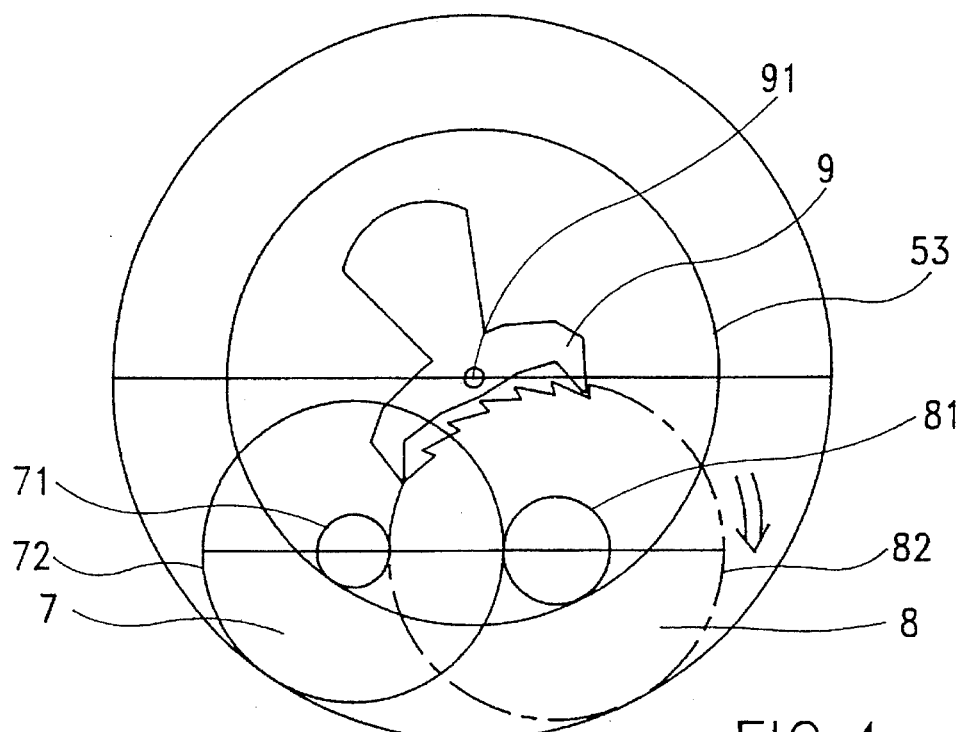
FIG. 4 is a bottom view of FIG. 3.
Figure 3:
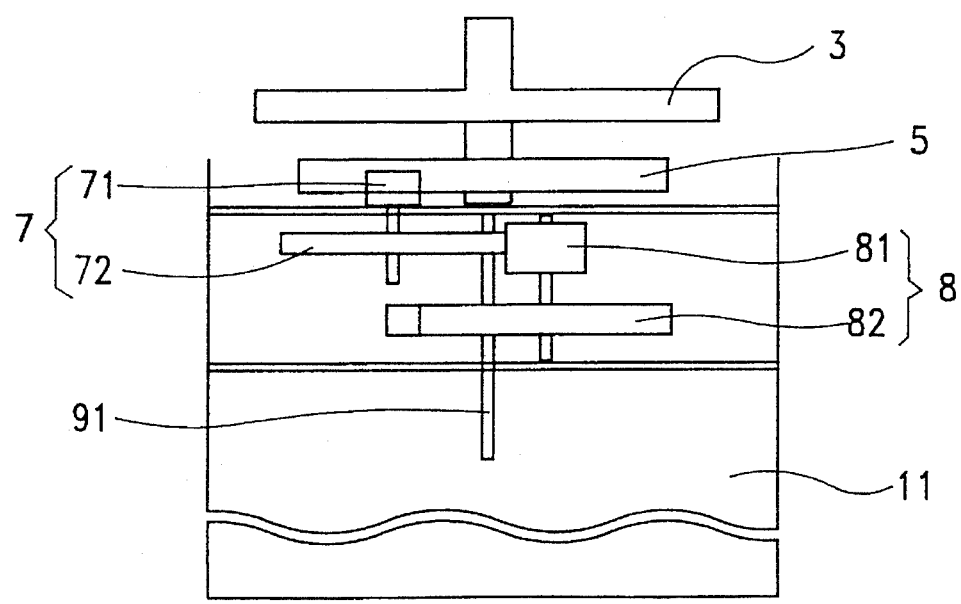
FIG. 3 is a sectional view showing the internal transmission mechanism of the contact lens cleaning apparatus of FIG. 2.

Referring to FIGS. 3 and 4, when the rotary knob 3 is turned in one direction, the clockwork 4 is turned tight to reserve energy. When the rotary knob 3 is released from the hand, the driving rod 31 of the rotary knob 3 is turned in the reversed direction to rotate the rotary wheel 5, causing the internal gear 52 of the rotary wheel 5 to turn the first gear set 7 and then the second gear set 8. When the ratchet wheel 82 of the second gear set 8 is rotated by the first gear set 7 through the pinion 81, the driven pawl 9 is forced to oscillate the shaft 91, causing the lens cage 10 oscillated in the cleaning solution inside the container 11.

Figure 5:
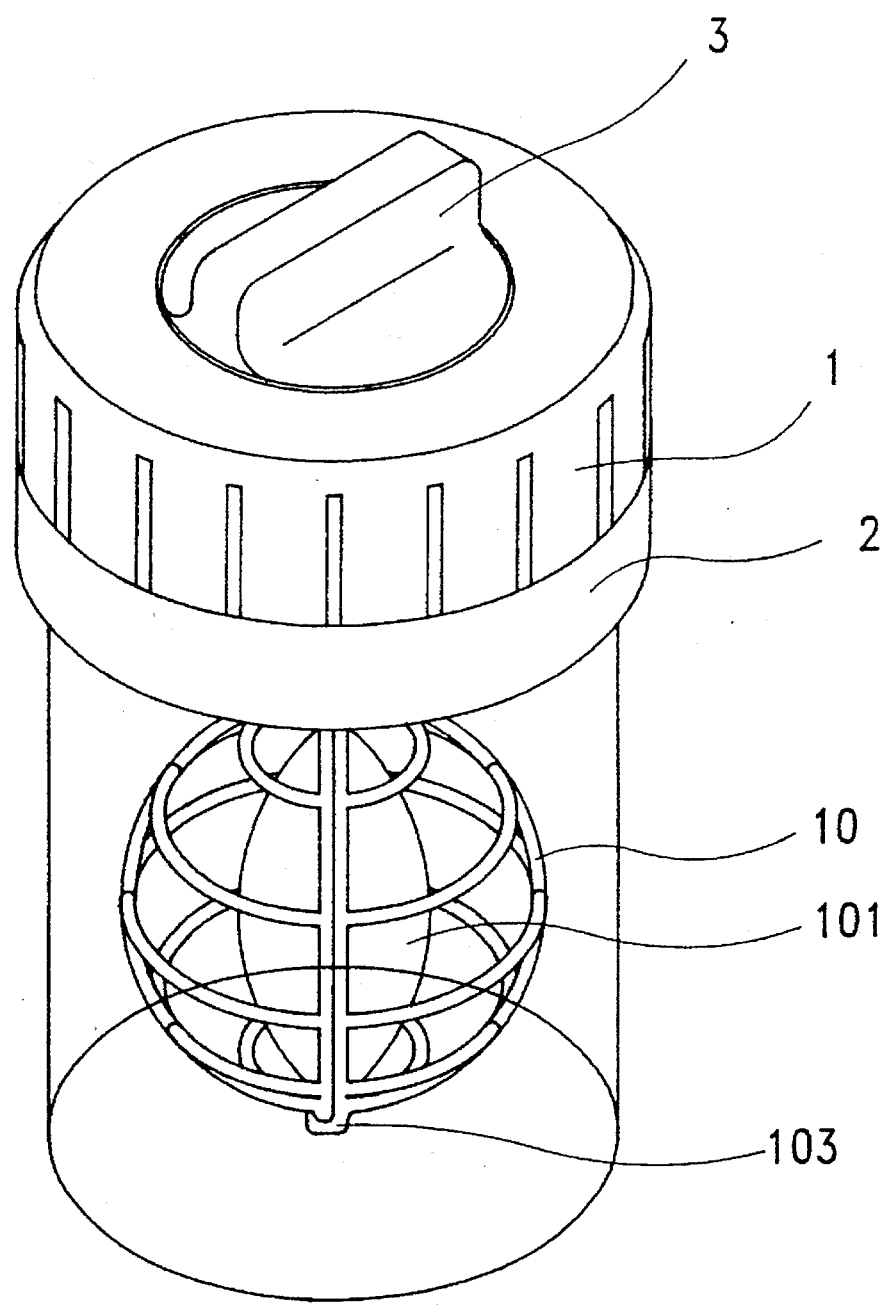
FIG. 5 is a perspective elevation of the contact lens cleaning apparatus of FIG. 2.

Referring to FIG. 5, when the lens cage 10 is closed, the fastener 103 is fastened up to hold the lens cage 19 in the closed position. Because the lens cage 10 is comprised of two semispherical gratings hinged together, they can be conveniently opened for loading the left eye contact lens and the right eye contact lens respectively.

What is claimed is:

1. A contact lens cleaning apparatus comprising a container to hold a cleaning solution, a bottom cover covered on said container, a top cover covered on said bottom cover, a lens cage connected to said bottom cover to hold contact lenses in said cleaning solution, and a transmission mechanism mounted within said bottom cover and said top cover and controlled by a rotary knob to oscillate said lens cage in said cleaning solution, wherein said transmission mechanism comprises:

a rotary wheel coupled to said rotary knob and having an internal gear at a bottom thereof;

a clockwork having a center tip fixed to said rotary knob and being operated to turn said rotary wheel;

a locating board disposed between inside said bottom cover and covered by said rotary wheel, said locating board having a locating hole;

a first gear set mounted on said locating board and turned by said rotary wheel, said first gear set comprising a pinion meshed with said internal gear and having a gear shaft inserted through the locating hole on said locating board, and a big gear fixedly mounted around the gear shaft of the pinion of said first gear set;

a second gear set mounted within said bottom cover and covered by said locating board, said second gear set comprising a pinion meshed with the big gear of said first gear set and having a gear shaft, and a ratchet wheel fixedly mounted around the gear shaft of the pinion of said second gear set;

a driven pawl meshed with said ratchet wheel; and a shaft coupled to said driven pawl and inserted through a hole on said bottom cover and then coupled to said lens cage.

2. The contact lens cleaning apparatus of claim 1 wherein said lens cage comprises two symmetrical semispherical gratings hinged together for holding the left eye contact lens and the right eye contact lens respectively, and a fastener connected to said gratings for fastening them in a closed position.

* * * * *